United States Patent
Karim et al.

(10) Patent No.: US 6,258,992 B1
(45) Date of Patent: Jul. 10, 2001

(54) GAS PHASE CATALYTIC OXIDATION OF HYDROCARBONS TO CARBOXYLIC ACIDS AND DEHYDROGENATED PRODUCTS

(75) Inventors: Khalid Karim; Asad Khan, both of Riyadh (SA)

(73) Assignee: Saudi Basic Industries Corporation (SA)

( * ) Notice: Subject to any disclaimer, the term of this patent is extended or adjusted under 35 U.S.C. 154(b) by 0 days.

(21) Appl. No.: 09/399,275

(22) Filed: Sep. 17, 1999

(51) Int. Cl.$^7$ .................. C07C 5/333; C07C 51/215; C07C 51/25; C07C 51/305
(52) U.S. Cl. .................. 585/663; 585/328; 585/658; 562/547; 562/548; 562/549; 560/245
(58) Field of Search ..................... 585/328, 658, 585/663; 562/547, 548, 549; 560/245

(56) References Cited

U.S. PATENT DOCUMENTS

| | | | |
|---|---|---|---|
| 2,423,418 | 7/1947 | Stone et al. | 260/630 |
| 2,720,550 | 10/1955 | Danforth | 260/668 |
| 2,867,677 | 1/1959 | Murray | 260/673.5 |
| 3,403,192 | * 9/1968 | Vadekar et al. . | |
| 3,456,026 | * 7/1969 | Cohen . | |
| 3,585,248 | * 6/1971 | Pasternak et al. . | |
| 3,585,249 | * 6/1971 | Cohen et al. . | |
| 3,585,250 | * 6/1971 | Pasternak et al. . | |
| 3,666,687 | * 5/1972 | Croce et al. . | |
| 3,970,697 | 7/1976 | Scheben et al. | 260/533 |
| 4,148,757 | 4/1979 | Brazdil et al. | 252/423 |
| 4,188,490 | 2/1980 | Hinnenkamp et al. | 560/245 |
| 4,250,346 | 2/1981 | Young et al. | 585/658 |
| 4,339,355 | 7/1982 | Decker et al. | 252/464 |
| 4,370,492 | 1/1983 | Wunder et al. | 560/245 |
| 4,524,236 | 6/1985 | McCain | 585/658 |
| 4,568,790 | 2/1986 | McCain | 585/658 |
| 4,596,787 | 6/1986 | Manyik et al. | 502/312 |
| 4,899,003 | 2/1990 | Manyik et al. | 585/313 |
| 4,902,823 | 2/1990 | Wunder et al. | 560/245 |
| 5,185,308 | 2/1993 | Bartley et al. | 502/170 |
| 5,405,996 | * 4/1995 | Suzuki et al. . | |
| 5,907,056 | * 5/1999 | Karim et al. . | |
| 6,013,597 | * 1/2000 | Karim et al. . | |
| 6,028,221 | * 2/2000 | Karim et al. . | |
| 6,040,474 | * 3/2000 | Jobson et al. . | |
| 6,060,421 | * 5/2000 | Karim et al. . | |
| 6,087,297 | * 7/2000 | Karim et al. . | |
| 6,143,921 | * 11/2000 | Karim et al. . | |
| 6,180,821 | * 1/2001 | Jobson et al. . | |

FOREIGN PATENT DOCUMENTS

| | | |
|---|---|---|
| 627401 | 12/1993 | (EP) . |
| WO/98/05620 | 2/1998 | (WO) . |
| WO/99/13980 | 3/1999 | (WO) . |

* cited by examiner

Primary Examiner—Jerry D. Johnson
(74) Attorney, Agent, or Firm—Kramer Levin; Naftalis & Frankel LLP

(57) ABSTRACT

Lower hydrocarbons are converted to carboxylic acids and/or dehydrogenated hydrocarbon product by contacting a feed mixture containing lower hydrocarbons, oxygen source, diluent, and sulfur-containing compound, with a multifunctional, mixed metal catalyst at a temperature from about 150° C. up to about 400° C. The lower hydrocarbons include $C_2$–$C_4$, and the presence of sulfur compound in the feed mixture results in increased yield of carboxylic acid and/or dehydrogenated hydrocarbon product.

16 Claims, No Drawings

GAS PHASE CATALYTIC OXIDATION OF HYDROCARBONS TO CARBOXYLIC ACIDS AND DEHYDROGENATED PRODUCTS

BACKGROUND OF THE INVENTION

1. Field of Invention

This invention relates to processes for low temperature catalytic oxidation of lower hydrocarbon feed to carboxylic acids and dehydrogenated product, particularly the conversion of ethane/ethylene to acetic acid or direct oxidation of ethane to vinyl acetate monomer over mixed metal oxide catalysts. The feed includes sulfur containing compound capable of producing oxides of sulfur. The process achieves a high yield of partial oxidation products.

2. Description of the Related Art

Numerous processes are known for catalytic oxidation of ethane to oxygenated or oxy-dehydrogenated products. For example, U.S. Pat. No. 3,970,697, European Patent 627,401, European Patent Application 480,594 and International Application WO 99/13980 describe catalysts and processes for the production of acetic acid from ethane and ethylene. U.S. Pat. Nos. 4,250,346, 4,524,236, 4,568,790, 4,596,787 and 4,899,003 describe catalysts and processes for oxydehydrogenation of ethane to ethylene. U.S. Pat. Nos. 4,370,492, 5,185,308, 4,902,823.and International Application WO 98/05620 describe catalysts and processes for the production of vinyl acetate from ethylene, acetic acid and oxygen. U.S. Pat. No. 4,339,355 describes catalysts and processes for the production of acrylic acid from acrolein. U.S. Pat. No. 4,148,757 describes catalysts for the ammoxidation of olefins to acrylonitrile and for the oxidation of olefins to acrolein and acrylic acid. In order to increase activity and product selectivity, most of the catalytic systems described in these disclosures include the addition of promoting metals to the catalysts rather than any process gas or co-feed as a promoter.

Oxidative dehydrogenation is a well known process for converting saturated or partially saturated organic compounds to corresponding compounds containing a greater degree of unsaturation. Yields of the reaction products are related to the type of the catalyst system and to the process conditions. Oxidative dehydrogenation processes utilizing sulfur oxide are described in U.S. Pat. Nos. 4,188,490 and 3,970,697. The catalysts used in the processes of U.S. Pat. Nos. 4,188,490 and 3,970,697 include palladium and gold on supports such as zinc oxide, alumina and silica; the catalyst is pre-treated with sulfur compound in moist air so that the concentration of sulfur-containing modifier is from about 0.05% to about 25% of the pre-treated, zinc oxide supported palladium and gold catalyst composition.

In U.S. Pat. Nos. 2,867,677, 2,423,418 and 2,720,550, sulfur dioxide is added in alkane dehydrogenation reactions which are run at very high temperatures above 400° C. to 700° C. where total oxidation products become dominant. Consequently, the yields of the desired product are rather low. Moreover, organic sulfide compounds formed as by products are adsorbed on the surface of the catalysts and hinder the overall reaction.

Accordingly, it would be desirable to provide a low temperature method which can have a significant impact on the productivity of the required products without effecting the integrity of the mixed metal oxide catalysts.

OBJECTS OF THE INVENTION

It is an object of the invention to overcome the above-identified deficiencies.

It is another object of the invention to provide a low temperature catalytic method yielding high productivity of oxygenated product.

It is another object of the invention to provide a low temperature catalytic method yielding high productivity of dehydrogenated products.

It is a further object of the invention to provide an improved catalytic method for the oxidation of lower alkanes to corresponding acids and aldehydes.

It is a further object of the invention to provide an improved catalytic method for the oxidation of alkanes to produce corresponding carboxylic acids, aldehydes and dehydrogenated products, using sulfur-containing compounds having at least two oxygens as promoters.

It is another object of the invention to produce vinyl acetate monomer (VAM) directly through ethane oxidation using sulfur containing compounds as a promoters in the presence of mixed metal oxide catalyst at particular process conditions.

Other objects as well as aspects, features and advantages of the present invention will become apparent from a study of the present specification, including the claims and specific examples.

SUMMARY OF THE INVENTION

The process of the present invention is a low temperature catalytic process for the production of oxygenated/oxydehydrogenated products by vapor phase oxidation of lower hydrocarbons using a small amount of sulfur-containing compounds such as hydrogen sulfide, sulfur dioxide or carbonyl sulfide in the feed. The process is carried out in the presence of multi-component, mixed metal redox catalysts. The invention using sulfur compounds in the feed can also be utilized in oxidation/ammoxidation of propane/propylene and direct production of vinyl acetate monomer from the conversion of ethane to ethylene followed by oxidation of ethylene with acetic acid.

Other objects as well as aspects, features and advantages of the present invention will become apparent from a study of the present specification, including the claims and specific examples.

DESRIPTION OF THE PREFERRED EMBODIMENTS

The invention relates to a low temperature catalytic process, where a reactant feed comprising alkane ($C_2$, $C_3$, $C_4$), oxygen, sulfur-containing compound such as hydrogen sulfide, sulfur dioxide or carbonyl sulfide, and optionally water, is contacted in a vapor phase with a mixed metal oxide catalyst preferably having a composition selected from (i) A calcined composition of $Mo_aV_bNb_cX_d$, wherein X=P, B, Hf, Te, As, or mixture thereof, and wherein a is 1 to 5, b is >0 to 0.1, c is 0.01 to 0.5, and d is >0 to 0.1.

The numerical values a, b, c and d represent the relative gram-atom ratios of the elements, Mo, V, Nb and X, respectively, in the catalyst. The elements are preferably present in combination with oxygen in the form of various oxides. This composition is described in U.S. Pat. No. 6,013,597 which is herein incorporated by reference.

(ii) A calcined composition of $Mo_aV_bNb_cPd_d$, wherein
a is 1 to 5,
b is 0 to 0.5,
c is 0.01 to 0.5, and
d is 0 to 0.045.

The numerical values a, b, c and d represent the relative gram-atoms ratios of the elements, Mo, V, Nb and Pd, respectively, in the catalyst. The elements are preferably present in combination with oxygen in the form of various oxides. This composition is described in U.S. Pat. No. 5,907,056 which is herein incorporated by reference.

(iii) A calcined composition of $Mo_aV_bLa_cPd_dNb_eX_f$, wherein X=Al, Ga, Ge, Si, (at least one element), and wherein
a is 1,
b is 0.01 to 0.9,
c is 0> to 0.2,
d is 0> to 0.2,
e is 0> to 0.2, and
f is 0> to 0.3.

The numerical values a, b, c, d, e and f represent the relative gram-atom ratios of the elements, Mo, V, La, Pd, Nb and X, respectively, in the catalyst. The elements are preferably present in combination with oxygen in the form of various oxides. This composition is described in U.S. Pat. No. 6,060,421.

(iv) A calcined composition of $Mo_aV_bPd_cLa_d$, wherein
a is 1 to 5,
b is 0.01 to 0.9,
c 0> to 0.5, and
d 0> to 0.045.

This composition is described in U.S. Pat. No. 6,087,297 which is herein incorporated by reference.

(v) A calcined composition of $Mo_aV_bGa_cPd_dNb_eX_f$, wherein X=at least one or more from La, Te Ge, Zn, Si, In, W, Bi, W, Mn, Sb, Sn, Fe, Co, Ni, Re, Rh, Pb, Cu, Au, Ti, Na, K, Rb, Mg, Ca, B, and wherein
a is 1,
b is 0.01 to 0.9,
c is 0> to 0.2,
d is 0> to 0.2,
e is 0> to 0.2, and
f is 0> to 0.5.

The numerical values of a, b, c, d, e and f represent the relative gram-atom ratios of the elements Mo, V, Ga, Pd, Nb and X respectively, in the catalyst. The elements are present in combination with oxygen in the form of various oxides. This composition is described in U.S. Pat. No. 6,114,278 which is herein incorporated by reference.

(vi) A calcined composition of $Mo_aV_bLa_cPd_dNb_eX_f$, wherein: X=Cu or Cr or both, and wherein
a is 1,
b is 0.01 to 0.9,
c is 0> to 0.2,
d is 0.0000001 to 0.2,
e is 0 to 0.2, and
f is 0 to 0.2.

The numerical values of a, b, c, d, e and f represent the relative gram-atom ratios of the elements Mo, V, La, Pd, Nb and X respectively, in the catalyst. The elements are present in combination with oxygen in the form of various oxides. This composition is described in U.S. Pat. No. 6,143,928 which is herein incorporated by reference.

The catalysts of the invention can be used with or without a support. Suitable supports for the catalyst include porous materials such as micro/meso/nanoporous materials or molecular sieve materials. Support materials include, e.g., alumina, silica, titania, zirconia, zeolites, silicon carbide, carbon such as activated charcoal, Mo carbide, molecular sieves and other micro/nanoporous materials, and mixtures thereof When used on a support, the supported catalyst usually comprises from about 10 to 50% by weight of the catalyst composition, with the remainder being the support material.

Hydrocarbon feedstock is oxidized with molecular oxygen and co-feed sulfur-containing compound to yield corresponding dehydrogenated and acid products. The process is carried out in a gas phase reaction at a temperatures of 150° C. to $_{400}$° C. and at a pressures of 1–50 bar, or 15 to 500 psi, for a contact time between reaction mixture and catalyst from 0.1 second to about 60 seconds.

The feed mixture includes from about 5% to about 95% by volume of lower hydrocarbons, particularly $C_2$ to $C_4$, more particularly, ethane, ethylene, propane, propylene, butane, butylene or mixtures thereof. In carrying out the process the reaction mixture generally contains one mole of hydrocarbon ($C_2$, $C_3$, $C_4$), 0.01 to 2.0 moles of molecular oxygen either as pure oxygen or in the form of air, and zero to 4.0 moles of water in the form of steam. Oxygen sources for the feed include purified oxygen, air and oxygen enriched air, depending on the economics of separation and the hydrocarbon conversion achieved. The ratio of hydrocarbon ($C_2$–$C_4$) to oxygen varies with the desired conversion and the selectivity of the catalyst, but generally is in the range of 1/5 to 5/1. The feed mixture can include molecular oxygen in an amount ranging from zero to 50% by volume of the feed mixture. Reaction can also be preferably effected in the presence of diluents such as inert gases, e.g., argon, helium, nitrogen, or steam. Inert gas diluents can be used in an amount from about 5% to about 90% by volume. Steam can be used in an amount from zero up to about 40% by volume. The ratio of hydrocarbons ($C_2$–$C_4$) to diluents can be in the range 1/5 to 1/1. The water vapor or steam is used as a reaction diluent and as a heat moderator for the reaction, and it also acts as desorption accelerator of the reaction product in the vapor phase oxidation reaction. Other gases which may be used as reaction diluent or heat moderators include, e.g., helium, nitrogen, and carbon dioxide.

Sulfur containing compounds can act as a promoter and can be added to the reaction zone as a gas or liquid with water. The concentration of the sulfur containing compound can range from 0.05 to about 10%, preferably about 0.05% to about 5% volume, more preferably about 0.06 to 3% by volume of the feed mixture. The preferred sulfur compounds used in this invention have at least two oxygen atoms, and can have three to four atoms of oxygen associated with each sulfur atom. Preferred sulfur promoters include COS, $SO_2$, $SO_3$, $H_2SO_4$, sulfurous acids, sulfonic acid or inorganic and organic acid of sulfur. In the case of $H_2S$, the active sulfur species can be formed in situ over the surface of the (redox) catalysts by the reaction of $H_2S$ and oxidizing agent such as mobile or adsorbed oxygen.

The gaseous components of the reaction mixture include a non-explosive mixture of $C_2$–$C_4$ hydrocarbons, oxygen or oxygen and diluents, and these components are preferably uniformly admixed prior to being introduced into the reaction zone. The components may be preheated, individually or after being admixed, prior to being introduced into the reaction zone. The reaction zone generally has a pressure of from 1 to 50 bar, preferably from 1 to 30 bar and a temperature of from about 150° C. to about 400° C. A preferred pressure range in terms of psi is about 50 to about 500 psi. Contact time between the reaction mixture and the catalyst is from about 0.01 second to 100 seconds, preferably about 0.1 second to about 60 seconds, more preferably from about 0. 1 second to about 10 seconds; at a space hourly velocity from about 50 to about 50,000 $hr^{-1}$, preferably from about 100 to about 10,000 $hr^{-1}$ and most preferably from about 200 to about 3,000 $hr^{-1}$.

The liquid products of the reaction can be separated from the unreacted feed hydrocarbons by condensation or by scrubbing, usually with water or dilute acid.

The process can be carried out in a single stage or in multiple stages of two or more, and can include intermediate stages where, for example, additional reactants can be fed or reaction conditions such as temperature and/or pressure can be adjusted.

In one embodiment of the invention, a mixture comprising ethane, steam, sulfur-containing compound and oxygen or a compound capable of providing oxygen in the presence of mixed metal oxide catalysts, are reacted in a first reaction zone to provide a stoichiometric first product mixture comprising ethylene, oxygen, steam and acetic acid in high productivity. The first product mixture is fed into a second reaction zone in which the ethylene and acetic acid react in the presence of vinyl acetate monomer (VAM) catalyst to form vinyl acetate. The VAM catalyst can be chosen from VAM catalysts conventional in the art. The first product mixture can be fed directly into the second reaction zone without adding additional components, or the first product mixture can be adjusted by the addition of ethylene, acetic acid or oxygen. Moreover, the first product mixture can be subjected to temperature and/or pressure adjustment prior to being fed into the second reaction zone.

EXAMPLES

The following examples are illustrative of some of the products and methods of making the same falling within the scope of present invention. They are, of course, not to be considered in any way limitative of the invention. Numerous changes and modifications can be made without departing from the spirit of the invention.

Catalytic oxidation processes using the mixed metal oxide catalyst and co-feed of sulfur promoter were carried out in a tubular reactor. All experiments were run at a temperature of 280° C. and a pressure of about 200 psi.

Gaseous reaction products were analyzed on-line by gas chromatography. Oxygen, nitrogen, $H_2S$, COS and carbon monoxide were analyzed using a 3-mm by 3 mm column of 13x molecular sieve. Carbon monoxide, ethane, ethylene, propane, propylene, butane, butylenes, and water were analyzed using a 1.8 m by 3 mm column packed with material sold under the tradename HAYASEP™ Q. Liquid products containing carboxylic acids and aldehydes were analyzed using a 0.5 m by 3 mm column packed with material sold under the trademark PORAPACK™ N.

Example 1

Calcined mixed metal oxide catalyst with a composition $Mo_1V_{0.398}La_{7.08e-6}Pd_{01.90e-04}Nb_{0.125}Al_{0.226}$ was prepared and formulated into uniform particles of the 40–60 mesh size. Catalyst was evaluated at a temperature of 280° C./200 psi with feed mixture containing ethane:oxygen:nitrogen:$H_2S$:COS in a proportion of 40:8:52:0:0. Reaction product showed the following results:

Ethane conversion (mol %): 9.89
Ethylene selectivity (%): 10
Acetic acid selectivity (%): 66
COx (%): 24
Ethylene yield(%): 0.99
Acetic acid yield (%): 6.52

Overall reaction showed a 7.51% yield to partial oxidation product and 2.37% to COx total oxidation product.

Example 2

Calcined mixed metal oxide catalyst with a composition $Mo_1V_{0.398}La_{7.08e-6}Pd_{01.90e-04}Nb_{0.125}Al_{0.226}$ was prepared and formulated into uniform particles of the 40–60 mesh size. Catalyst was evaluated at a temperature of 280° C./200 psi with feed mixture containing ethane: oxygen: nitrogen:$H_2S$:COS in a proportion of 40:8:51:0.6:0.40. Reaction product showed the following results:

Ethane conversion (mol %): 17
Ethylene selectivity (%): 41
Acetic acid selectivity (%): 45
COX(%) 14
Ethylene yield (%): 7
Acetic acid yield (%): 7

Overall reaction showed a 14.62% yield to partial oxidation product and 2.38% to COx total oxidation product.

Catalytic data demonstrate that a small concentration of sulfur containing compound yields a high productivity of partial oxidation product in reactions over mixed metal oxide catalysts at low temperature. This low temperature catalytic process is applicable for the oxidation or ammoxidation of other hydrocarbons such as propane and butane. Furthermore, this high productivity process can also applied as a first stage process for the production of equal molar amounts of ethylene and acetic acid from ethane and then feeding the reactor outlet product to a vinyl acetate monomer (VAM) reactor containing conventional Pd/Au catalyst or mixed metal oxide catalysts for the production of VAM.

We claim:

1. A gas phase process for the catalytic oxidation of hydrocarbons to carboxylic acids and dehydrogenated product said process comprising contacting a feed mixture comprising hydrocarbons selected from the group consisting of $C_2$, $C_3$ and $C_4$ alkanes and alkenes and mixtures thereof, oxygen, diluent and sulfur-containing compound with a mixed metal oxide catalyst, said contacting at a temperature of 150° C. to 400° C., under conditions sufficient for gas phase oxidation.

2. The process of claim 1 wherein the hydrocarbons are selected from the group consisting of $C_2$, $C_3$ and $C_4$ hydrocarbons and mixtures thereof.

3. The process of claim 1 where the mixed metal oxides catalyst is selected from the group consisting of i) a calcined composition comprising $Mo_aV_bNb_cX_d$, wherein X equals P, B, Hf, Te, As or mixture thereof, and wherein:
  a is 1 to 5,
  b is >0 to 0.1,
  c is 0.01 to 0.5,
  d is >0 to 0.1, and the numerical values a, b, c and d represent the relative gram-atom ratios of the elements, Mo, V, Nb and X respectively in the catalyst;

(ii) a calcined composition comprising $Mo_aV_bNb_cPd_d$ wherein:
a is 1 to 5,
b is 0 to 0.5,
c is 0.01 to 0.5, and
d is 0 to 0.045, and the numerical values a, b, c and d represent the relative gram-atoms ratios of the elements Mo, V, Nb and Pd respectively in the catalyst;

(iii) a calcined composition comprising $Mo_aV_bLa_cPd_dNb_eX_f$, wherein: X equals at least one element of Al, Ga, Ge, Si, and wherein:
a is 1,
b is 0.01 to 0.9,
c is 0> to 0.2,
e is 0> to 0.2,
f is 0> to 0.3, and the numerical values a, b, c, d, e and f represent the relative gram-atom ratios of the elements Mo, V, La, Pd, Nb and X respectively, in the catalyst;

(iv) a calcined composition comprising $Mo_aV_bPd_cLa_d$, wherein:
a is 1 to 5,
b is 0.01 to 0.9,
c 0> to 0.5,
d 0> to 0.045, (v) a calcined composition comprising $Mo_aV_bGa_cPd_dNb_eX_f$, wherein X equals at least one of La, Te Ge, Zn, Si, In, W, Bi, W, Mn, Sb, Sn, Fe, Co, Ni, Re, Rh, Pb, Cu, Au, Ti, Na, K,Rb, Mg, Ca, B, and wherein:
a is 1,
b is 0.01 to 0.9,
c is 0> to 0.2,
d is 0> to 0.2,
e is 0> to 0.2,
f is 0> to 0.5, and the numerical values of a, b, c, d, e and f represent the relative gram-atom ratios of the elements Mo, V, Ga, Pd, Nb and X respectively in the catalyst and these elements are present in combination with oxygen in the form of oxides; or (vi) a calcined composition comprising $Mo_aV_bLa_c$, $Pd_dNb_eX_f$, wherein X equals Cu or Cr or both, and wherein:
a is 1,
b is 0.01 to 0.9,
c is 0> to 0.2,
d is 0.0000001 to 0.2,
e is 0 to 0.2,
f is 0 to 0.2, and the numerical values of a, b, c, d, e and f represent the relative gram-atom ratios of the elements Mo, V, La, Pd, Nb and X respectively in the catalyst.

4. The process of claim 3 wherein said catalysts are supported on porous material comprising molecular sieves, SiC, MoC, titania, zirconia, silica or alumina.

5. The process of claim 1, wherein said feed mixture comprises molecular oxygen in an amount from 0.1 to 50% by volume of the feed mixture.

6. The process of claim 1, wherein said feed mixture diluent comprises an inert gas comprising $N_2$, He or Ar in an amount from about 5% to about 90% by volume.

7. The process of claim 1, wherein said feed mixture diluent comprises steam in an amount up to 40% by volume.

8. The process of claim 1, wherein said feed mixture comprises sulfur containing compound as a promoter in an amount from about 0.05 to about 5% by volume of the feed mixture.

9. The process of claim 8, wherein the said sulfur containing compounds are selected from the group consisting of $SO_2$, $SO_3$, $H_2S$, COS, sulfurous acid and sulfonic acid.

10. The process of claim 1, wherein said feed mixture comprises from about 5% to about 95% by volume of lower hydrocarbons selected from the group consisting of ethane, ethylene, propane, propylene, butanes, butylene and mixture thereof.

11. The process of claim 1, wherein said conditions sufficient for gas phase oxidation comprise a pressure from about 15 to about 500 psi, and a contact time between feed mixture and catalyst of from about 0.1 second to about 60 seconds.

12. The process of claim 1, wherein the process is carried out in a reaction zone comprising single stage, multiple stages or multiple stages with intermediate stage(s) and wherein oxidant is fed to the reaction zone at single stage, multi stage or intermediate stage of the reaction zone.

13. The process of claim 1, wherein said process comprises reacting ethane with steam, sulfur-containing compound and oxygen or a compound capable of providing oxygen, in the presence of mixed metal oxide catalysts in a first reaction zone to produced a stoichiometric first product mixture comprising ethylene, oxygen, steam and acetic acid, and said first product mixture is fed into a second reaction zone wherein the ethylene and acetic acid react to form vinyl acetate in the presence of vinyl acetate monomer producing catalyst.

14. The process of claim 13 wherein said first product mixture is fed directly into said second reaction zone without adding additional components.

15. The process of claim 13, wherein said first product mixture is fed into said second reaction zone with addition or adjustment of amounts of ethylene or acetic acid or oxygen.

16. The process of claim 13, wherein said mixture is subjected to temperature and/or pressure adjustment prior to being fed into said second reaction zone.

* * * * *